US006331659B1

(12) United States Patent
Wakayama et al.

(10) Patent No.: US 6,331,659 B1
(45) Date of Patent: Dec. 18, 2001

(54) CUMULUS CELLS AS NUCLEAR DONORS

(75) Inventors: Teruhiko Wakayama; Ryuzo Yanagimachi, both of Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/132,104

(22) Filed: Aug. 10, 1998

Related U.S. Application Data

(60) Provisional application No. 60/089,940, filed on Jun. 19, 1998, and provisional application No. 60/072,002, filed on Jan. 21, 1998.

(51) Int. Cl.⁷ .......................... C12N 15/00; A01K 67/00
(52) U.S. Cl. .................................. 800/24; 800/14; 800/8
(58) Field of Search ...................... 800/8, 13, 24

(56) References Cited

U.S. PATENT DOCUMENTS

| | | |
|---|---|---|
| 4,994,384 | 2/1991 | Prather et al. . |
| 5,057,420 | 10/1991 | Massey . |
| 5,480,772 | 1/1996 | Wangh . |
| 5,496,720 | 3/1996 | Susko-Parrish et al. . |
| 5,651,992 | 7/1997 | Wangh . |
| 5,773,217 | 6/1998 | Wangh . |
| 5,945,577 * | 1/2000 | Stice et al. ............................. 800/24 |
| 6,011,197 * | 1/2000 | Stice et al. ............................. 800/24 |

FOREIGN PATENT DOCUMENTS

| | | |
|---|---|---|
| 2092258 | 7/1994 | (CA) . |
| 2092258 A1 | 7/1994 | (CA) . |
| 0 559 307 | 9/1993 | (EP) . |
| WO 95/16770 | 6/1995 | (WO) . |
| WO 95/17500 | 6/1995 | (WO) . |
| WO 96/07732 | 3/1996 | (WO) . |
| WO 97/07668 | 3/1997 | (WO) . |
| WO 97/07669 | 3/1997 | (WO) . |
| WO 97/37009 | 10/1997 | (WO) . |
| WO 98/07841 | 2/1998 | (WO) . |
| WO 98/30683 | 7/1998 | (WO) . |
| WO 99/01163 | 1/1999 | (WO) . |
| WO 99/01164 | 1/1999 | (WO) . |

OTHER PUBLICATIONS

Fulka, J. et al. Cloning by somatic cell nuclear transfer. *Bioessays* 20:847–851 (1998).

VanStekelenburg–Hamers, A.E.P. et al. Nuclear Transfer and Electrofusion in Bovine in Vitro–Matured/In Vitro–Fertilized Embryos: Effect of Media and Electrical Fusion Parameters. *Molecular Reproduction and Development* 36: 307–312 (1993).

Liu, L. et al. Nuclear transfer in sheep embryos: the effect of cell cycle coordination between nucleus and cytoplasm and the use of in vitro matured oocytes. *Molecular Reproduction and Development* 47: 255–264 (1997).

Matthews, J.B. et al. Effects of F–actin stabilization or disassembly on epithelial Cl–secretion and Na–K–2Cl cotransport. *American Journal of Physiology* 272: 254–262 (1997).

Smith, L.C. et al. Influence of nuclear and cytoplasmic activity on the development in vivo of sheep embryos after nuclear transplantation. *Biology of Reproduction* 40: 1027–1035 (1989).

Stice, S.L. et al. Bovine nuclear transfer embryos: oocyte activation prior to blastomere fusion. *Molecular Reproduction and Development* 38:61–68 (1994).

Eppig, John J. Intercommunication between mammalian oocytes and companion somatic cells. *BioEssays* 13, No. 11, 569–573 (1991).

Bos–Mikich, A., et al. Meiotic and Mitotic $Ca^{2+}$ oscillations affect cell composition in resulting blastocysts. *Dev. Biol.* 182, 172–179 (1997).

Campbell, K.H.S., et al. Cell cycle co–ordination in embryo cloning by nuclear transfer. *Rev. Reprod.* 140–45 (1996).

Campbell, K.H.S., et al. Sheep cloned by nuclear transfer from a cultured cell line. *Nature* 380, 64–66 (1996).

Chatot, C.L., et al. Development of 1–cell embryos from different strains of mice in CZB medium. *Biol. Reprod.* 42, 432–440 (1990).

Collas, P. & Barnes, F. L. Nuclear transplantation by microinjection of inner cell mass and granulosa cell nuclei. *Mol. Reprod. Dev.* 38, 264–267 (1994).

Czolowska, R., et al. Behavior of thymocyte nuclei in non–activated and activated mouse oocytes. *J. Cell Sci.* 69, 19–34 (1984).

Dietrich, W., et al. A genetic map of the mouse suitable for typing intraspecific crosses. *Genetics* 131, 423–447 (1992).

Eppig, J., et al. Murine oocytes suppress expression of luteinizing hormone receptor messenger ribonucleic acid by granulosa cells. *Biol. Reprod.* 56, 976–984 (1997).

Erickson, R. P., Zwigman, T. & Ao, A. Gene expression, X–inactivation, and methylation during spermatogenesis: the case of *Zfa*, *Zfx*, and *Zfy* in mice. *Mol. Reprod. Dev.* 35, 114–120 (1993).

(List continued on next page.)

*Primary Examiner*—Deborah Crouch
(74) *Attorney, Agent, or Firm*—Jones, Day, Reavis & Pogue

(57) ABSTRACT

Animals are produced following injection of adult somatic cell nuclei into enucleated oocytes. The invention provides a method for cloning an animal by directly inserting at least a portion of the adult somatic nucleus (including the minimum chromosomal material able to support development) into a recipient enucleated oocyte. Preferably, the nucleus is inserted by microinjection and, more preferably, by piezo electrically-actuated microinjection. The oocyte is activated prior to, during, or up to about 6 hours after insertion of the nucleus, by electroactivation or exposure to a chemical activating agent, such as $Sr^{2+}$. The activated renucleated oocyte is allowed to develop into an embryo and is transplanted to a host surrogate mother to develop into a live offspring.

22 Claims, 4 Drawing Sheets

(1 of 4 Drawing Sheet(s) Filed in Color)

OTHER PUBLICATIONS

Johnson, K.R., Cook, S.A. Davisson, M.T. Chromosomal localization of the murine gene and two related sequcnes encoding high–mobility–group I and Y proteins. *Genomics* 12, 503–509 (1992).

Kimura, Y. & Yanagimachi, R. Intracytoplasmic sperm injection in the mouse. *Biol. Reprod.* 52, 709–720 (1995).

Kimura, Y. & Yanagimachi, R. Mouse oocytes injected with testicular spermatozoa or round spermatidescan develop into normal offspring. *Development* 121, 2397–2405 (1995).

Kono, T. Nuclear transfer and reprogramming. *Rev. Reprod.* 1, 40–45 (1996).

Kono, T., Ogawa, M. & Nakahara, T. Thymocyte transfer to enucleated oocytes in the mouse. *J. Reprod. Dev.* 39, 301–307 (1993).

Kono, T., Sotomaru, Y., Sato, Y. & Nakahara, T. Development of androgenetic mouse embryos produced by in vitro fertilization of enucleated oocytes. *Mol. Reprod. Dev.* 34, 43–46 (1993).

Kuretake, S., Kimura, Y., Hoshi, K. & Yanagimachi, R. Fertilization and development of mouse oocytes injected with isolated sperm–heads. *Biol. Reprod.* 55, 789–795 (1996).

Kwon, O.Y. and Kono, T. Production of identical sextuplet mice by transferring metaphase nuclei from four–cell embryos. *PNAS* 93, 13010–13013 (1996).

McGrath, J. & Solter, D. Inability of mouse blastomere nuclei transferred to enucleated zygotes to support development in vitro. *Science* 226, 1317–1319 (1984).

Schnieke, A., et al. Human factor IX transgenic sheep produced by transfer of nuclei from transfected fetal fibroblasts. *Science* 278, 2130–2133 (1997).

Schuetz, A. W., Whittingham, D. G. & Snowden, R. Alterations in the cell cycle of mouse cumulus granulosa cells during expansion and mucification in vivo and in vitro. *Reprod. Fertil. Dev.* 8, 935–943 (1996).

Taylor, B.A. & Rowe, L. A mouse linkage testing stock possessing multiple copies of the endogenous ecotropic murine leukemia virus genome. *Genomics* 5,221–232 (1989).

Tsunoda, T., et al. Nuclear transplantation of male primordial germ cells in the mouse. *Development* 107, 407–411 (1989).

Tsunoda, T. & Kato, Y. Nuclear transplantation of embryonic stem cells in mice. *J. Reprod. Fertil.* 98, 537–540 (1993).

Wakayama, T., Perry, A.C.F., Zuccotti, M., Johnson, K.R. & Yanagimachi, R. Full–term development of mice from enucleated oocytes injected with cumulus cell nuclei. *Nature* 394, 369–374 (1998).

Willadsen, S.M. Nuclear transplantation in sheep embryos. *Nature* 320, 63–65 (1986).

Wilmut, I., et al. Viable offspring derived from fetal and adult mammalian cell. *Nature* 385, 810–813 (1997).

Yanagida, K., et al. Thermostability of sperm nuclei assessed by microinjection into hamstet oocytes. *Biol. Reprod.* 44, 440–447 (1991).

Wolf et al (1998) J. Biotech. 65, 99–110.*

Summers et al (1995) Biol. Reproduc. 53, 431–437.*

Manseau et al (1996) Develp. 122, 2109–2116.*

* cited by examiner

A. *D1Mit46*

B. *D2Mit102*

C. *Emv* loci 1 2 3 4 5 6 7 8 9 10 11 12 13 14 15 16 17 18 19 20

CUMULUS CELLS AS NUCLEAR DONORS

This application claims the benefit of U.S. Provisional Patent Applications, Serial No. 60/072,002, filed Jan. 21, 1998, and Serial No. 60/089,940, filed Jun. 19, 1998.

The U.S. Government has a paid-up license in this invention and the right in limited circumstances to require the patent owner to license others on reasonable terms as provided for by the terms of contract No. R01-HD03402 awarded by the National Institutes of Health, Public Health Service.

BACKGROUND OF THE INVENTION

The invention relates to the cloning of animals by the insertion of a nucleus of an adult somatic cell into an enucleated oocyte in such a way that the host oocyte forms an embryo and can develop into a live animal. In one embodiment of the invention, insertion of a nucleus is accomplished by piezo electrically-actuated microinjection.

The rapid production of large numbers of near-identical animals is very desirable. For example, it is expected that broad medical benefits may be obtained when the near-identical animals are also genetically engineered (e.g., transgenic) animals. Genetically altered large animals can act as living pharmaceutical "factories" by producing valuable pharmaceutical agents in their milk or other fluids or tissue (a production method sometimes referred to as "pharming") or act as living organ or cell "factories" for human organs or cells that will not be rejected by the human immune system. The production of large numbers of near-identical research animals, such as mice, guinea pigs, rats, and hamsters is also desirable. For example, the mouse is a primary research model for the study of mammalian biology, and the availability of near-identical, transgenic or non-transgenic, mice would be very beneficial in the analysis of, for example, embryonic development, human diseases, and for testing of new pharmaceuticals. Thus, for a variety of reasons, (e.g., in the context of breeding farm animals, or the interpretation of data generated in mice), it may be desirable to reliably produce offspring of a particular animal that are genetically near-identical to the parent.

Further, with respect to transgenesis, current protocols for generating transgenic animals are not sufficiently advanced to guarantee the programmed control of gene expression in the context of the whole animal. Although it is possible to minimize detrimental "position" effects caused by the quasi-random manner in which the transgene integrates into the host genome, differences can exist in transgene expression levels between individuals carrying the same transgene construct inserted at the same locus in the same copy number. Thus, generating even modest numbers of transgenic animals producing the desired levels of any given recombinant protein(s) can be very time-consuming and expensive. These problems may be exacerbated because the number of transgenic offspring is often low (commonly only one) due to low efficiency, and many transgenic founders are infertile.

One approach to solving these problems is to "clone" genetically near-identical animals from the cells of transgenic or non-transgenic adult animals that have a desired trait or produce a target product at the desired level. To this end, colonies of genetically near-identical animals (clones) could be generated relatively rapidly from the cells of a single adult animal. Moreover, selective and reliable cloning of adult animals that produce increased yields of milk and meat could rapidly produce large numbers of high producers. Cloning of animals from adult somatic cells could also be beneficial in the reproduction of pets (e.g., dogs, cats, horses, birds, etc.) and rare or endangered species. As used herein, "cloning" refers to the full development to adulthood of an animal whose non-mitochondrial DNA may be derived from a somatic donor cell through the transfer of nuclear chromosomes from the somatic donor cell to a recipient cell (such as an oocyte) from which the resident chromosomes have been removed.

In normal mammalian development, oocytes become developmentally arrested at the germinal vesicle (GV) stage in prophase of the first meiotic division. Upon appropriate stimulation (e.g., a surge in plasma luteinizing hormone), meiosis resumes, the germinal vesicle breaks down, the first meiotic division is completed and the oocyte then becomes arrested at metaphase of the second meiosis ("Met II"). Met II oocytes can then be ovulated and fertilized. Once fertilized, the oocyte completes meiosis with the extrusion of the second polar body and the formation of male and female pronuclei. The embryos begin to develop by undergoing a series of mitotic divisions before differentiating into specific cells, resulting in the organization of tissues and organs. This developmental program ensures the successful transition from oocyte to offspring.

Although the cells of early embryos have classically been regarded as totipotent (that is, that they are capable of developing into a new individual per se), this totipotency is lost following a small number of divisions, that number varying between species (e.g., murine and bovine embryos). The mechanisms underlying this apparent loss of totipotency are poorly understood but are presumed to reflect subtle changes in the DNA environment affecting gene expression, that are collectively termed "reprogramming". Without being bound by theory, it is believed that cloning techniques could possibly either subvert or mimic "reprogramming".

Given the enormous practical benefits of cloning, there has been a commensurately great interest in overcoming technological barriers and developing new a techniques for the fusion of either embryonic cells or fetal cells with enucleated oocytes. To date, however, there has been a lack of reported protocols that have reproducibly generated full term development of clones from adult somatic cells. For example, it has been reported that when bovine cumulus cell nuclei were injected into enucleated oocytes which were then electro-activated, 9% of 351 injected oocytes developed to blastocysts, but none developed to term. Likewise, Sendai virus-mediated fusion of adult mouse thymocytes with enucleated Met II oocytes, followed by activation thirty to sixty minutes later with 7% ethanol, resulted in 75% of 20 oocytes reaching the 2-cell stage, but none developed beyond the 4-cell stage.

A recent report describes the electrofusion of cultured "mammary gland cells" with enucleated oocytes to produce a single live offspring sheep, which was named "Dolly" (Wilmut, I. et al. (1997), Nature 385, 810–813). Dolly is reported to have developed from one of 434 enucleated oocytes electrofused with cells derived from the mammary gland that had been cultured for five days under conditions of serum starvation. According to the method reported to have been used to clone Dolly, the "mammary gland cell" was inserted by micropipette into the perivitelline space of an enucleated oocyte. Wilmut reports that the cells were immediately subjected to an electric pulse to induce membrane fusion and activate the oocyte to trigger resumption of the cell cycle. The resulting embryo (in addition to 28 others in the experiment) was transferred into a suitable recipient and, in this single case, the pregnancy proceeded to produce Dolly. However, because the "mammary gland cell" was from a cell line established from a 6-year old sheep that was in the third trimester of pregnancy, doubt has been publicly expressed as to the identity of the cells from which the donor nucleus was obtained, and even whether that cell was of adult origin.

In view of the foregoing, a controllable and efficient method of cloning animals from adult somatic cells is highly desirable. The present invention provides a novel method to achieve this.

SUMMARY OF THE INVENTION

The invention provides a method for cloning an animal from an adult somatic cell by directly inserting the nuclear contents of the somatic cell (or a portion of the nuclear contents including at least the minimum chromosomal material able to support development) into the cytoplasm of an enucleated oocyte, and facilitating embryonic development of the resulting cell to term and beyond. As used herein, the term "adult somatic cell" means a cell from a post-natal animal, which is therefore neither a fetal cell nor an embryonic cell, and which is not of the gamete lineage. The resulting viable offspring is a clone of the animal that originally provided the somatic cell nucleus for injection into the oocyte. The invention is applicable to cloning of all animals, including amphibians, fish, birds (e.g., domestic chickens, turkeys, geese, and the like) and mammals, such as primates, ovines, bovines, porcines, ursines, felines, canines, equines, rodents, and the like.

In one embodiment of the invention, the donor adult somatic cell is "2n"; that is, it possesses the diploid complement of chromosomes as seen in G0 or G1 of the cell cycle. The donor cell may be obtained from an in vivo source or may be from a cultured cell line. An example of an in vivo source of the 2n donor nucleus (i.e., in G0 or G1 phase ) is a cumulus cell. Cumulus (Latin for "a little mound") cells are so-called because they form a solid mass (heap) of follicular cells surrounding the developing ovum prior to ovulating. Following ovulation in some species, such as mice, many of these cells remain associated with the oocyte (to form the cumulus oophorus) and, in mice, more than 90% are in G0/G1 and, therefore, are 2n. The invention contemplates using donor nuclei taken from other in vivo or in vitro (i.e., cultured) sources of 2n adult somatic cells including, without limitation, epithelial cells, neural cells, epidermal cells, keratinocytes, hematopoietic cells, melanocytes, chondrocytes, lymphocytes, macrophages, monocytes, nucleated erythrocytes, fibroblasts, Sertoli cells, cardiac muscle cells, skeletal muscle cells, smooth muscle cells, and other cells from organs including, without limitation, skin, lung, pancreas, liver, kidney, urinary bladder, stomach, intestine, bone, and the like, and their progenitor cells where appropriate.

In another embodiment of the invention, the donor adult somatic cell is "2–4C"; that is, it contains one to two times the diploid genomic content, as a result of replication during S phase of the cell cycle. This donor cell may be obtained from an in vivo or an in vitro source of actively dividing cells including, but not limited to, epithelial cells, hematopoietic cells, epidermal cells, keratinocytes, fibroblasts, and the like, and their progenitor cells where appropriate.

An embodiment of the method of the invention includes the steps of (i) allowing the nucleus (or portion thereof including the chromosomes) to be in contact with the cytoplasm of the enucleated oocyte for a period of time (e.g., up to about 6 hours) after insertion into the oocyte, but prior to activation of the oocyte, and (ii) activating the oocyte. In this embodiment, the nucleus is inserted into the cytoplasm of the enucleated oocyte by a method that does not concomitantly activate the oocyte.

When a donor nucleus having 2n chromosomes is employed, the method further includes the step of disrupting microtubule formation and/or actin filament formation for the period of time after insertion of the nucleus into the enucleated oocyte in order to suppress the formation of a polar body and maintain the 2n chromosome number. When, for example, a 4n donor nucleus is employed, this step of the method is omitted such that a polar body is formed, and the ploidy of the renucleated oocyte can be reduced to 2n.

In a preferred embodiment of the invention, the nucleus is inserted by microinjection and, more preferably, by piezo electrically-actuated microinjection. The use of a piezo electric micromanipulator enables harvesting and injection of the donor nucleus to be performed with a single needle. Moreover, the enucleation of the oocyte and injection of the donor cell nucleus can be performed quickly and efficiently and, consequently, with less trauma to the oocyte than with previously reported methods, such as the fusing of the donor cell and oocyte mediated by fusion-promoting chemicals, by electricity or by a fusogenic virus.

The introduction of nuclear material by microinjection is distinct from cell fusion, temporally and topologically. By the microinjection method, the plasma membrane of the donor cell is punctured (to enable extraction of the nucleus) in one or more steps that are temporally separated from delivery of that nucleus (or a portion thereof including at least the chromosomes) into an enucleated oocyte, also following plasma membrane puncture. Separate puncturing events are not a feature of cell fusion.

Furthermore, the spatiotemporal separation of nucleus removal and introduction allows controlled introduction of materials in addition to the nucleus. The facility to remove extraneous cytoplasm and to introduce additional materials or reagents may be highly desirable. For example the additive(s) may advantageously modulate the embryological development of the renucleated oocyte. Such a reagent may comprise an antibody, a pharmacological signal transduction inhibitor, or combinations thereof, wherein the antibody and/or the inhibitor are directed against and/or inhibit the action of proteins or other molecules that have a negative regulatory role in cell division or embryonic development. The reagent may include a nucleic acid sequence, such as a recombinant plasmid or a transforming vector construct, that may be expressed during development of the embryo to encode proteins that have a potential positive effect on development and/or a nucleic acid sequence that becomes integrated into the genome of the cell to form a transformed cell and a genetically altered animal. The introduction of a reagent into a cell may take place prior to, during, or after the combining of a nucleus with an enucleated oocyte.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 3A is a photomicrograph of the uteri of recipient females 8.5 days post coitum (dpc), fixed with Bouin's fluid, dehydrated and cleared with benzyl benzoate. All uterine implantation sites failed to develop except in one (arrow) where an embryo (FIG. 3b) appeared normal and was in the circa 12 somite stage.

FIG. 4A illustrates PCR typing using the strain-specific marker D1Mit46.

FIG. 4B illustrates PCR typing using the strain-specific marker D2Mit102. PCR-amplified DNA (FIG. 4A and FIG. 4B) from F1 hybrid mice exhibit an additional gel band not seen in DNA from the inbred parental strains (lanes 16–20). This extra band corresponds to a heteroduplex derived from the two parental products, whose conformation results in anomalous gel migration.

FIG. 4C illustrates Southern blot typing of strain-specific Emv loci (Emv1, Emv2 and Emv3).

FIG. 5 is a schematic representation of the cloning procedure of the present invention.

DETAILED DESCRIPTION OF THE INVENTION

Figure 1:
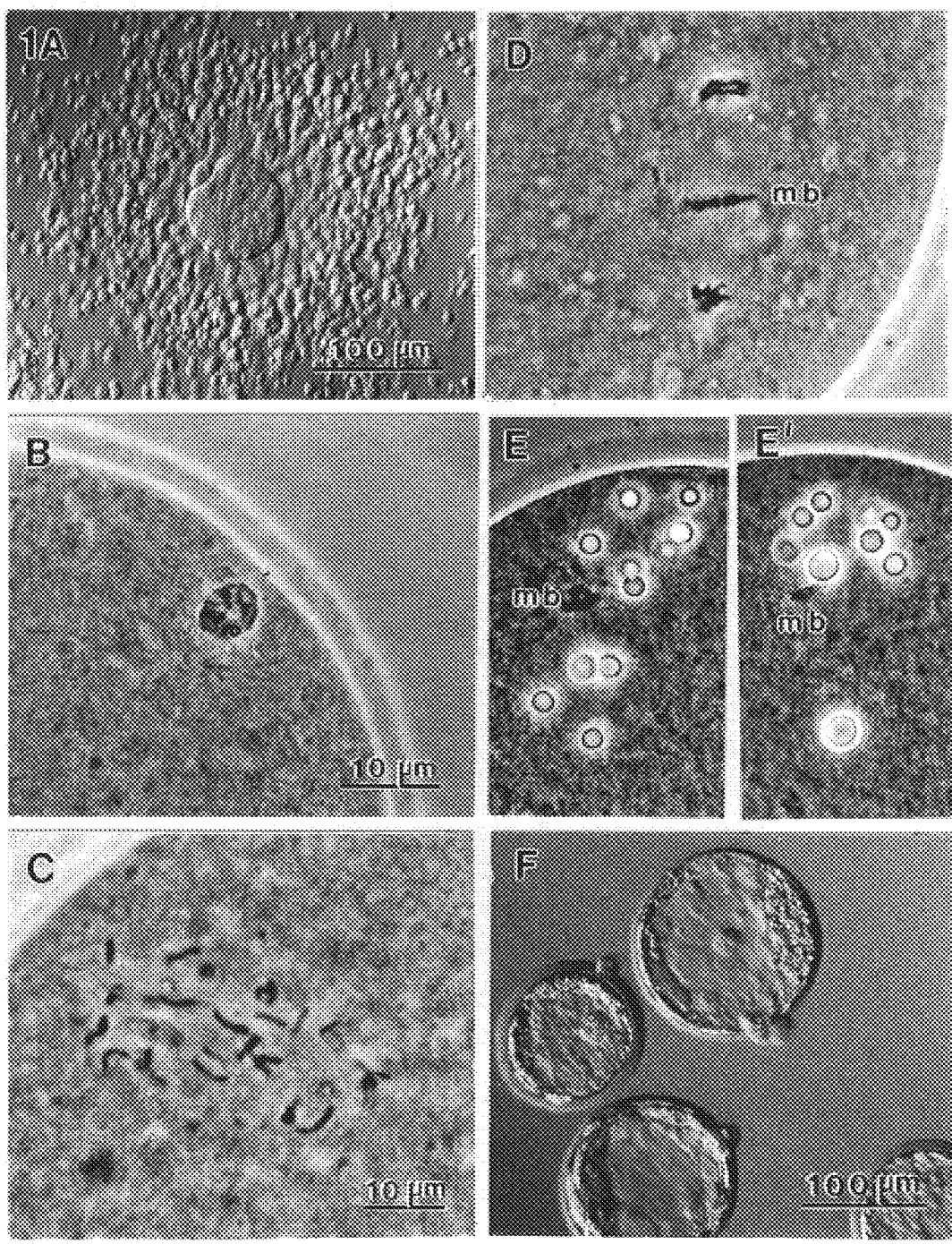
FIG. 1A is a photomicrograph of a live ovulated oocyte surrounded by cumulus cells. The egg coat, the zona pellucida, appears as a relatively clear zone around the oocyte.
FIG. 1B is a photomicrograph taken within 10 minutes after injection of a cumulus cell nucleus into the cytoplasm of an enucleated oocyte, showing the intact cumulus cell nucleus within the oocyte cytoplasm. Oocytes injected with cumulus cell nuclei were fixed, stained and photographed with a phase contrast microscope.
FIG. 1C is a photomicrograph showing transformation of the nucleus into apparently disarrayed chromosomes 3 hours after injection of the nucleus. The disarray reflects an unusual situation in which single, condensed chromatids are each attached to a single pole of the spindle, and are therefore not aligned on a metaphase plate.
FIG. 1D is a photomicrograph taken 1 hour after activation of the oocyte with $Sr^{2+}$ showing chromosomes segregated into two groups. (mb=midbody).
FIGS. 1E and 1E' are photomicrographs taken 5 hours after activation of the oocyte with $Sr^{2+}$ showing two pseudo-pronuclei with a varying number of distinct nucleolus-like structures discernable per egg. The size and number of pseudo-pronuclei varied, suggesting 'random' segregation of chromosomes following oocyte activation.
FIG. 1F is a photomicrograph of live blastocysts produced following injection of enucleated oocytes with cumulus cell nuclei.

The mitotic cell cycle ensures that every cell that divides donates equal genetic material to two daughter cells. DNA synthesis does not occur throughout the cell division cycle but is restricted to a part of it, namely the synthetic phase (or "S" phase) before mitosis. A gap of time (G2) occurs after DNA synthesis and before cell division; another gap (G1) occurs after division and before the next S phase. The cell cycle thus consists of the M (mitotic) phase, a G1 phase (the first gap), the S phase, a G2 phase (the second gap), and back to M. Many nondividing cells in tissues (for example, all resting fibroblasts) suspend the cycle after mitosis prior to S phase. Such "resting" cells which have exited from the cell cycle before S phase, are said to be in the G0 state. Cells entering G0 can remain in this state temporarily or for very long periods. Sertoli cells and neurons, for example, characteristically do not divide in adult animals but remain at G0. More than 90% of cumulus cells surrounding recently ovulated (mouse) oocytes are in G0 or G1. The nuclei of cells in G0 or G1 have a diploid (2n) DNA content, i.e., they have two copies of each morphologically distinct chromosome (of n-1 autosomal chromosome types). The nuclei of cells in G2 have a 4C DNA content, i.e., during S phase, DNA in each of the two copies of the each of the distinct chromosomes has been replicated.

The present invention describes a method for generating clones of vertebrate animals. In the method, each clone develops from an enucleated oocyte that has received the nucleus (or a portion thereof including, at least, the chromosomes) of an adult somatic cell. In one embodiment of the invention, cloned mice were born following microinjection of the nuclei of cumulus cells (i.e., ovulated ovarian follicle cells) into enucleated oocytes by the method of the invention. Additional animals such as, but not limited to, primates, cattle, pigs, cats, dogs, horses, and the like, may be also cloned by the method of the invention. The invention method is shown herein to provide a high rate of successful development of embryos to the morula/blastocyst stage, a high rate of implantation of transferred embryos in recipient foster mammals, and a greater than 2% success rate of resulting newborn mammals. The magnitude of these efficiencies means that the method of the invention is readily reproducible.

Steps and substeps of one embodiment of the method of the invention for cloning an animal are illustrated in the example of FIG. 5. Briefly, oocytes are harvested (1) from an oocyte donor animal and the Met II plate is removed (2) to form an enucleated oocyte (chromosomally "empty" egg). Somatic cells are harvested (3) from an adult donor, healthy-looking cells are selected (4), and their nuclei (or nuclear constituents including the chromosomes) are obtained (5). A single nucleus is injected (6) into the cytoplasm of an enucleated oocyte. The nucleus is allowed to reside within the cytoplasm of the enucleated oocyte (7) for up to 6 hours, during which time chromosome condensation may be observed. The oocyte is then activated (8) in the presence of an inhibitor of microtubule or actin filament formation (9) to suppress the formation of a polar body. During this activation time period, the formation of pseudo-pronuclei may be observed. Eggs forming pseudo-pronuclei are selected and placed in embryo culture (10). The embryos are then transferred (11) to foster surrogate mothers, to permit the birth (12) of live offspring.

Thus, one embodiment of the method of the invention for cloning a mammal comprises the following steps: (a) collecting a somatic cell nucleus, or a portion thereof containing at least the chromosomes, from a somatic cell of an adult mammal; (b) inserting the at least that portion of the somatic cell nucleus into an enucleated oocyte to form a renucleated oocyte; (c) allowing the renucleated oocyte to develop into an embryo; and (d) allowing the embryo to develop into a live offspring. Each of these steps is described below in detail. The somatic cell nucleus (or nuclear constituents containing the chromosomes) may be collected from a somatic cell that has greater than 2n chromosomes (e.g., one which has one to two times the normal diploid genomic content). Preferably, the somatic cell nucleus is collected from a somatic cell that has 2n chromosomes. Preferably, the somatic cell nucleus is inserted into the cytoplasm of the enucleated oocyte. The insertion of the nucleus is preferably accomplished by microinjection and, more preferably, by piezo electrically-actuated microinjection.

Activation of the oocyte may take place prior to, during, or after the insertion of the somatic cell nucleus. In one embodiment, the activation step takes place from zero to about six hours after insertion of the somatic cell nucleus in order to allow the nucleus to be in contact with the cytoplasm of the oocyte for a period of time prior to activation of the oocyte. Activation may be achieved by various means including, but not limited to, electroactivation, or exposure to ethyl alcohol, sperm cytoplasmic factors, oocyte receptor ligand peptide mimetics, pharmacological stimulators of $Ca^{2+}$ release (e.g., caffeine), $Ca^{2+}$ ionophores (e.g., A2318, ionomycin), modulators of phosphoprotein signaling, inhibitors of protein synthesis, and the like, or combinations thereof. In one embodiment of the invention, the activation is achieved by exposing the cell to strontium ions ($Sr^{2+}$).

Activated, renucleated oocytes injected with 2n chromosomes are preferably exposed to a microtubule or actin filament disrupting agent (described below) to prevent the formation of a polar body, thus retaining all the chromosomes of the donor nucleus within the renucleated host oocyte. Activated, renucleated oocytes injected with 2–4C nuclei are preferably not exposed to such an agent, in order to allow the formation of a polar body to reduce the number of chromosomes to 2n.

The step of allowing the embryo to develop may include the substep of transferring the embryo to a female mammalian surrogate recipient, wherein the embryo develops into a viable fetus. The embryo may be transferred at any stage, from two-cell to morula/blastocyst stage, as known to those skilled in the art.

Embodiments of the present invention may have one or more of the following advantages, as well as other advantages not listed. First, nucleus delivery (or delivery of nuclear constituents including the chromosomes) by microinjection is applicable to a wide variety of cell types—whether grown in vitro or in vivo—irrespective of size, morphology, developmental stage of donor, and the like. Second, nucleus delivery by microinjection enables careful control (e.g., minimization) of the volume of nucleus donor cell cytoplasm and nucleoplasm introduced into the enucleated oocyte at the time of nuclear injection, as extraneous material may "poison" developmental potential. Third, nucleus delivery by microinjection allows carefully controlled co-injection (with the donor nucleus) of additional agents into the oocyte at the time of nuclear injection. These are exemplified below. Fourth, nucleus delivery by microinjection allows a period of exposure of the donor nucleus to the cytoplasm of the enucleated oocyte prior to activation.

This exposure may allow chromatin remodeling/reprogramming which favors subsequent embryonic development. Fifth, nucleus delivery by microinjection allows a wide range of choices for subsequent activation protocol (in one embodiment, the use of $Sr^{2+}$). Different activation protocols may exert different effects on developmental potential. Sixth, activation may be in the presence of microtubule-disrupting agents (in one embodiment, cytochalasin B) to prevent chromosome extrusion, and modifiers of cellular differentiation (in one embodiment, dimethylsulfoxide) to promote favorable developmental outcome. Seventh, in one embodiment, nucleus delivery is by piezo electrically-actuated microinjection, allowing rapid and efficient processing of samples and thereby reducing trauma to cells undergoing manipulation. This is, in part, because somatic nucleus preparation and introduction into the enucleated oocyte may be performed with the same injection needle (in contrast to conventional microinjection protocols which require at least one change of injection needle between coring of the zona pellucida and puncturing of the oocyte plasma membrane). Moreover, the oocytes of some species (e.g., mouse) are not amenable to microinjection using conventional needles, whereas piezo electrically-actuated microinjection affords a high success rate. Finally, not only individual steps in the present invention, but their relationship to each other as a whole, results in a high cloning efficiency. We now present those individual steps in greater detail and show how they are arranged in respect of one to the other in the present invention.

The Recipient Oocytes.

The stage of in vivo maturation of the oocyte at enucleation and nuclear transfer has been reported to be significant to the success of nuclear transfer methods. In general, reports of mammalian nuclear transfer describe the use of Met II oocytes as recipients. Met II oocytes are of the type normally activated by fertilizing spermatozoa. It is known that the chemistry of the oocyte cytoplasm changes throughout the maturation process. For example, a cytoplasmic activity associated with maturation, metaphase-promoting factor ("MPF"), is maximal in immature oocytes at metaphase of the first meiotic division ("Met I"), declining with the formation and expulsion of the first polar body ("Pb1"), and again reaching high levels at Met II. MPF activity remains high in oocytes arrested at Met II, rapidly diminishing upon oocyte activation. When a somatic cell nucleus is injected into the cytoplasm of a Met II oocyte (i.e., one with high MPF activity), its nuclear envelope breaks down and chromatin condenses, resulting in the formation of metaphase chromosomes.

Oocytes that may be used in the method of the invention include both immature (e.g., GV stage) and mature (i.e., Met II stage) oocytes. Mature oocytes may be obtained, for example, by inducing an animal to super-ovulate by injections of gonadotrophic or other hormones (for example, sequential administration of equine and human chorionic gonadotrophins) and surgical harvesting of ova shortly after ovulation (e.g., 80–84 hours after the onset of estrous in the domestic cat, 72–96 hours after the onset of estrous in the cow and 13–15 hours after the onset of estrous in the mouse). Where it is only possible to obtain immature oocytes, they are cultured in a maturation-promoting medium until they have progressed to Met II; this is known as in vitro maturation ("IVM"). Methods for IVM of immature bovine oocytes are described in WO 98/07841, and for immature mouse oocytes in Eppig & Telfer (*Methods in Enzymology* 225, 77–84, Academic Press, 1993).

Oocyte Enucleation

Preferably, the oocyte is exposed to a medium containing a microtubule disrupting agent or actin depolymerizing agent prior to and during enucleation. Disruption of the microfilaments imparts relative fluidity to the cell membrane and underlying cortical cytoplasm, such that a portion of the oocyte enclosed within a membrane can easily be aspirated into a pipette with minimal damage to cellular structures. One microtubule-disrupting agent of choice is cytochalasin B (5 $\mu$g/mL). Other suitable microtubule-disrupting agents, such as nocodazole, 6-dimethylaminopurine and colchicine, are known to those skilled in the art. Actin depolymerizing agents are also known and include, but are not limited to, cytochalasin D, jasplakinolide, latrunculin A, and the like.

In one preferred embodiment of the invention, the enucleation of the Met II oocyte is achieved by aspiration using a piezo electrically-actuated micropipette. Throughout the enucleation microsurgery, the Met II oocyte is anchored by a conventional holding pipette and the flat tip of a piezo electrically-driven enucleation pipette (internal diameter $\approx 7$ $\mu$m) is brought into contact with the zona pellucida. A suitable piezo electric driving unit is sold under the name of Piezo Micromanipulator/Piezo Impact Drive Unit by Prime Tech Ltd. (Tsukuba, Ibaraki-ken, Japan). The unit utilizes the piezo electric effect to advance, in a highly controlled, rapid manner, the (injection) pipette holder a very short distance (approximately 0.5 $\mu$m). The intensity and interval between each pulse can be varied and are regulated by a control unit. Piezo pulses (for example, intensity=1–5, speed=4–16) are applied to advance (or drill) the pipette through the zona pellucida while maintaining a small negative pressure within the pipette. In this way, the tip of the pipette rapidly passes through the zona pellucida and is thus advanced to a position adjacent to the Met II plate (discernible as a translucent region in the cytoplasm of the Met II oocytes of several species, often lying near the first polar body). Oocyte cytoplasm containing the metaphase plate (which contains the chromosome-spindle complex) is then gently and briskly sucked into the injection pipette in a minimal volume and the injection pipette (now containing the Met II chromosomes) withdrawn slightly. The effect of this procedure is to cause a pinching off of that part of the oocyte cytoplasm containing the Met II chromosomes. The injection pipette is then pulled clear of the zona pellucida, and the chromosomes are discharged into neighboring medium in preparation for microsurgical removal of chromosomes from the next oocyte. Where appropriate, batches of oocytes may be screened to confirm complete enucleation. For oocytes with granular cytoplasm (such as porcine, ovine and feline oocytes), staining with a DNA-specific fluorochrome (e.g., Hoeschst 33342) and brief examination with low UV illumination (enhanced by an image intensified video monitor) is advantageous in determining the efficiency of enucleation.

Enucleation of the Met II oocyte may be achieved by other methods, such as that described in U.S. Pat. No. 4,994,384. For example, enucleation may be accomplished microsurgically using a conventional micropipette, as opposed to a piezo electrically-driven a micropipette. This can be achieved by slitting the zona pellucida of the oocyte with a glass needle along 10–20% of its circumference close to the position of the Met II chromosomes (the spindle is located in the cortex of the oocyte by differential interference microscopy). The oocyte is placed in a small drop of medium containing cytochalasin B in a micromanipulation chamber. Chromosomes are removed with an enucleation pipette having an unsharpened, beveled tip.

After enucleation, the oocytes are ready to be reconstituted with adult somatic cell nuclei. It is preferred to prepare enucleated oocytes within about 2 hours of donor nucleus insertion.

Preparation of Adult Somatic Cell Nuclei

Cells derived from populations grown in vivo or in vitro and containing cells with 2n chromosomes (e.g., those in G0 or G1) or greater than 2C chromosomes (e.g., those in G2, which are normally 4C) may be suitable nuclear donors. In one embodiment of the invention, the cells are follicle (cumulus) cells harvested from an adult mammal and dispersed mechanically and/or enzymatically (e.g., by hyaluronidase). The resulting dispersed cell suspension may be placed in a micromanipulation chamber facilitating detailed examination, selection and manipulation of individual cells to avoid those with certain characteristics (e.g., exhibiting advanced stages of apoptosis, necrosis or division). Gentle and repeated aspiration of cells selected in this way causes breakage of plasma and nuclear membranes and allows the corresponding nucleus to be harvested and washed free of surplus cytoplasmic and nuclear material. Individually selected nuclei are then aspirated into an injection pipette, described below, for insertion into enucleated oocytes.

Other somatic cells that may be used as sources of nuclei include, without limitation, epithelial cells, neural cells, epidermal cells, keratinocytes, hematopoietic cells, melanocytes, chondrocytes, lymphocytes, macrophages, monocytes, nucleated erythrocytes, fibroblasts, Sertoli cells, cardiac muscle cells, skeletal muscle cells, smooth muscle cells, and other cells from organs including, without limitation, skin, lung, pancreas, liver, kidney, urinary bladder, stomach, intestine, and the like, (and, where appropriate, their progenitor cells), derived directly from in vivo sources, or following culture in vitro.

Insertion of Donor Nucleus into Enucleated Oocyte

Nuclei (or nuclear constituents including the chromosomes) may be injected directly into the cytoplasm of the enucleated oocyte by a microinjection technique. In a preferred method of injection of nuclei from somatic cells into enucleated oocytes, a piezo electrically-driven micropipette is used, in which one may essentially use the equipment and techniques described above (with respect to enucleation of oocytes), with modifications here detailed.

For example, an injection pipette is prepared, as previously described, such that it has a flat tip with an inner diameter of about 5 $\mu$m. The injection needle contains mercury near the tip and is housed in the piezo electrically-actuated unit according to the instructions of the vendor. The presence of a mercury droplet near the tip of the injection pipette increases the momentum and, therefore, penetrating capability. The tip of an injection pipette containing individually selected nuclei is brought into intimate contact with the zona pellucida of an enucleated oocyte and several piezo pulses (using controller setting scales of intensity 1–5, speed 4–6) are applied to advance the pipette while maintaining a light negative pressure within. When the tip of the pipette has passed through the zona pellucida, the resultant zona plug is expelled into the perivitelline space and the nucleus is pushed forward until it is near the tip of the pipette. The pipette tip is then apposed to the plasma membrane and advanced (toward the opposite face of the oocyte) until the holding pipette almost reaches the opposite side of the cortex of the oocyte. The oocyte plasma membrane is now deeply invaginated around the tip of the injection needle. Upon application of one to two piezo pulses (typically, intensity 1–2, speed 1), the oolemma is punctured at the pipette tip, as indicated by a rapid relaxation of the oolemma, which may be clearly visible. The nucleus is then expelled into the ooplasm with a minimum amount (about 6 pL) of accompanying medium. The pipette is then gently withdrawn, leaving the newly introduced nucleus within the cytoplasm of the oocyte. This method is performed briskly, typically in batches of 10–15 enucleated oocytes which at all other times are maintained in culture conditions.

Alternative microinjection variants, in which a conventional injection pipette is employed, may be used to insert the donor nucleus. An example of a suitable microinjection method employing a conventional pipette, for inserting sperm nuclei into hamster oocyte, is described in Yanagida, K., Yanagimachi, R., Perreault, S. D. and R. G. Kleinfeld, *Biology of Reproduction* 44, 440–447 (1991), the disclosure of which pertaining to such method is hereby incorporated by reference.

Activation of the Host Oocyte

In one embodiment of the invention, renucleated oocytes are returned to culture conditions for 0–6 hours prior to activation. Thus, in one embodiment of the invention, oocytes may be activated at any time up to approximately 6 hours (the latent period) after enucleation, either by electroactivation, injection of one or more oocyte-activating substances, or transfer of the oocytes into media containing one or more oocyte-activating substances.

Reagents capable of providing an activating stimulus (or combination of activating stimuli) include, but are not limited to, sperm cytoplasmic activating factor, and certain pharmacological compounds (e.g., $Ca^{2+}$ and other signal transduction modulators), which may be introduced by microinjection after, or concomitantly with, enucleation. Some activating stimuli are provided following transfer of renucleated oocytes (either immediately or following a latent period) to media containing one or members of a sub-set of activating compounds, including stimulators of $Ca^{2+}$ release (e.g., caffeine, $Ca^{2+}$ ionophores such as A 23187 and ionomycin, and ethanol), modulators of phosphoprotein signaling (e.g., 2-aminopurine, staurospurine, and sphingosine), inhibitors of protein synthesis (e.g., A 23187, cyclohexamide), 6-dimethylaminopurine, or combinations of the foregoing (e.g., 6-dimethylaminopurine and ionomycin). In one embodiment of the invention, activation of mouse oocytes is achieved by culture for 1–6 hours in $Ca^{2+}$-free CZB medium containing 2–10 mM $Sr^{2+}$.

In embodiments of the invention wherein the activation stimulus is applied concurrently with or after enucleation, renucleated oocytes are transferred to a medium containing one or more inhibitors of microtubule formation (e.g., 5 μg/mL cytochalasin B) or actin depolymerizing agents, such as those described above, to inhibit extrusion of chromosomes (via a "polar body") on or soon after application of the activating stimulus.

In one embodiment of the invention enucleated oocytes may be activated prior to enucleation. Activation methods may be as described above. Following exposure to an activating stimulus, oocytes may be cultured for up to approximately 6 hours prior to injection of a 2n somatic cell nucleus as described above. In this embodiment, somatically-derived chromosomes transform directly into pronucleus-like structures within the renucleated oocyte, and there is no need to suppress "polar body" extrusion by culture with a cytokinesis-preventing agent, such as cytochalasin-B.

Development of Embryos to Produce Viable Fetuses and Offspring

Following pronucleus formation, the embryo may be allowed to develop by culture in a medium that does not contain a microtubule disrupting agent. Culture may continue to the 2–8 cell stage or morula/blastocyst stage, at which time the embryo may be transferred into the oviduct or uterus of a foster mother.

Alternatively, the embryo may be split and the cells clonally expanded, for the purpose of improving yield. Alternatively or additionally, it may be possible for increased yields of viable embryos to be achieved by means of the present invention by clonal expansion of donors and/or if use is made of the process of serial (nuclear) transfer, whereby nuclear constituents from resulting embryos may be transferred back into an enucleated oocyte, according to the method of the invention described above, to generate a new embryo. In a further embodiment of the invention, the pronuclear embryo is cultured in vivo following direct transfer into a suitable recipient.

Modulation of Cell Division or Embryonic Development

In one embodiment of the invention, enucleation of an oocyte permits the introduction, prior to, during, or after the combining of a nucleus with the enucleated oocyte, of one or more agents with the potential to alter the developmental outcome of the embryo. Alternatively or additionally, the agent(s) may be introduced prior to or following enucleation. For example, nuclei may be co-injected with antibodies directed against proteins with hypothetical regulatory roles with the potential to influence the outcome of the method of the invention. Such molecules may include, but are not limited to, proteins involved in vesicle transport (e.g., synaptotagmins), those which may mediate chromatin-ooplasm communication (e.g., DNA damage cell cycle check-point molecules such as chk1), those with a putative role in oocyte signaling (e.g., STAT3) or those which modify DNA (e.g., DNA methyltransferases). Members of these classes of molecules may also be the (indirect) targets of modulatory pharmacological agents introduced by microinjection and which have roles analogous to those of antibodies. Both antibodies and pharmacological agents work by binding to their respective target molecules. Where the target has an inhibitory effect on developmental outcome, this binding reduces target function, and where the target has a positive effect on developmental outcome, the binding promotes that function. Alternatively, modulation of functions important in the cloning process may be achieved directly by the injection of proteins (e.g., those in the classes above) rather than agents which bind to them.

In a further embodiment of the invention ribonucleic acid (RNA) or deoxyribonucleic acid (DNA) may be introduced into the oocyte by microinjection prior to or following enucleation. For example, injection of recombinant DNA harboring the necessary cis-active signals may result in the transcription of sequences present on the recombinant DNA by resident or co-injected transcription factors, and subsequent expression of encoded proteins with an antagonistic effect on development inhibitory factors, or with a positive effect on embryo development Moreover, the transcript may possess antisense activity against mRNAs encoding development inhibitory proteins. Alternatively, antisense regulation may be achieved by injecting nucleic acids (or their derivatives) that are able to exert an inhibitory effect by interacting directly with their nucleic acid target(s) without prior transcription within the oocyte.

Recombinant DNA (linear or otherwise) introduced by the method of the invention may comprise a functional replicon containing one or more expressed, functional gene under the control of a promoter exhibiting anything from a narrow to a broad developmental expression profile. For example, the promoter might direct immediate, but brief expression where that promoter is active only in the early zygote. Introduced DNA may either be lost at some point during embryonic development, or integrate at one or more genomic loci, to be stably replicated throughout the life of the resulting transgenic individual. In one embodiment, DNA constructs encoding putative "anti-aging" proteins, such as telomerase or superoxide dismutase, may be introduced into the oocyte by microinjection. Alternatively, such proteins may be injected directly.

EXAMPLES

The following examples illustrate the method of the invention and the development of live offspring from oocytes injected with adult somatic cell nuclei. In particular, the examples illustrate the cloning of mice from enucleated oocytes injected with nuclei isolated from mouse cumulus cells, Sertoli cells, or neuronal cells. These somatic cell types have very distinctive morphologies, making them easy to identify confidently. The examples described herein are intended to be only examples of animal oocytes, adult somatic cells, and media that may be used in the process of the invention, and are not intended to be limiting, as other examples of embodiments of the invention would readily be recognized by those skilled in the art.

Reagents

All inorganic and organic compounds were purchased from Sigma Chemical Co. (St. Louis, Mo.) unless otherwise stated.

The medium used for culturing oocytes after microsurgery was CZB medium (Chatot, et al., 1989. *J. Reprod. Fert.* 86, 679–688), supplemented with 5.56 mM D-glucose. CZB medium comprises 81.6 mM NaCl, 4.8 mM KCl, 1.7 mM $CaCl_2$, 1.2 mM $MgSO_4$, 1.8 mM $KH_2PO_4$, 25.1 mM $NaHCO_3$, 0.1 mM $Na_2EDTA$, 31 mM Na.lactate, 0.3 mM Na.pyruvate, 7 U/mL penicillin G, 5 U/mL streptomycin sulfate, and 4 mg/mL bovine serum albumin. The medium for oocyte collection from oviducts, subsequent treatments and micromanipulation was a modified CZB containing 20 mM Hepes, a reduced amount of $NaHCO_3$ (5 mM) and bovine serum albumin at 3 mg/mL. This medium is herein termed Hepes-CZB. For microinjection purposes, it was preferred to replace the BSA in the Hepes CZB with 0.1 mg/mL polyvinyl alcohol (PVA, cold water soluble, average molecular mass $10 \times 10^3$) because PVA kept the wall of the injection pipette less sticky over a longer period of time than BSA and was beneficial during repeated use of a single pipette for multiple nuclei/oocyte transfers.

The medium used for isolation of brain cells was nucleus isolation medium (NIM), consisting of 123.0 mM KCl, 2.6 mM NaCl, 7.8 mM $NaH_2PO_4$, 1.4 mM $KH_2PO_4$, 3 mM $Na_2EDTA$. Its pH value was adjusted to 7.2 by addition of a small quantity of 1 M HCl. NIM supplemented with PVP (average molecular mass $3 \times 10^3$, ICN Biochemicals, Costa Mesa, Calif.) was used to suspend the brain cells prior to injection.

Animals

Animals used in these examples were maintained in accordance with the guidelines of the Laboratory Animal Service at the University of Hawaii and those prepared by the Committee on Care and Use of Laboratory Animals of the Institute of Laboratory Resources National Research Council (DHEW publication no. [NIH] 80-23, revised in 1985). The protocol of animal handling and treatment was reviewed and approved by the Animal Care and Use Committee at the University of Hawaii.

Example 1

Somatic Cell Preparation

In this example, cumulus cells from mouse oviducts were isolated for use as a source of adult somatic cell nuclei for injection into enucleated mouse oocytes. Derivations of the cloned mice produced in Series A–D of Table 2, and described below, are also described in Wakayama, et al., 1998, *Nature* 394, 369374.

Female B6D2F1 (C57BL/6×DBA/2 used in Series A and B), B6C3F1 (C57BL/6×C3H/He used in Series C) or B6C3F1 cloned mice produced in Series D were induced to superovulate by consecutive intravenous injections of 7.5 units of equine chorionic gonadotrophin (eCG) and 7.5 units of human chorionic gonadotrophin (hCG). Thirteen hours after hCG injection, cumulus-oocyte complexes (see FIG. 1A) were collected from oviducts and treated in Hepes-CZB medium supplemented with bovine testicular hyaluronidase (0.1% [w/v], 300 U/mg, ICN Biochemicals, Costa Mesa, Calif.) to disperse cumulus cells. Medium sized cumulus cells (10–12 μm in diameter) were the most commonly found (>70%) and these were selected for injection. Following dispersal, cells were transferred to Hepes-CZB containing 10% (w/v) polyvinylpyrrolidone (average molecular weight, 360,000 daltons) and retained at room temperature for up to 3 hours prior to injection.

Example 2

Somatic Cell Preparation

In this Example, Sertoli cells and brain cells (neurons) were isolated from adult mice. These cells characteristically do not divide in adult animals and remain permanently in G0 phase of the cell cycle.

Seminiferous tubules were isolated from the testis and exposed for 20 minutes at 30° C. to a solution of 1 mg collagenase per ml of Hepes-CZB. Tubules were then minced with a razor blade and placed in Hepes-CZB containing trypsin at 1 mg/ml with occasional agitation. The resultant suspension was then allowed to stand. The Sertoli cell rich fraction settled first. Suspended cells were removed by aspiration and fresh medium used to resuspend the remainder. Sertoli cells, with characteristic morphological features, are readily identifiable under low power microscopy. Manipulation of individual Sertoli cells was performed using a large injection pipette (inner diameter ≈10 pm).

Neuronal cells were isolated from the cerebral cortex of adult B6D2F1 females. Brain tissue was removed with sterile scissors, quickly washed in erythrocyte-lysing buffer and gently hand-homogenized for a few seconds in nucleus isolation medium (NIM) at room temperature. Nuclei harboring a conspicuous nucleolus were individually collected from the resulting suspension using the injection pipette, prior to delivery into a recipient enucleated oocyte.

Example 3

Insertion of Nuclei into Enucleated Oocytes

In this Example, murine Met II oocytes were harvested, enucleated, and subsequently microinjected with nuclei isolated from the cells of Examples 1 and 2, using a piezo electrically-actuated micropipette.

Enucleation of the oocytes was achieved by aspiration with a piezo electric-driven micropipette using the Piezo Micromanipulator Model MB-U by Prime Tech Ltd. (Tsukuba, Ibaraki-ken, Japan). This unit uses the piezo electric effect to advance the pipette holder a very short distance (approximately 0.5 μm) at a time at a very high speed. The intensity and speed of the pulse were regulated by the controller.

B6D2F1 oocytes (obtained 13 hours post hCG injection of eCG-primed females) were freed from the cumulus oophorous and held in CZB medium at 37.5° C. under approximately 5% (v/v) $CO_2$ in air until required. Groups of oocytes (usually 10–15) were transferred into a droplet of Hepes-CZB containing 5 μg/mL cytochalasin B, which had previously been placed in the operation chamber on the microscope stage. Oocytes undergoing microsurgery were held with a holding pipette and the zona pellucida 'cored' following the application of several piezo-pulses to an enucleation pipette.

The Met II chromosome-spindle complex (identifiable as a translucent region) was aspirated into the pipette with a minimal volume of oocyte cytoplasm. Following enucleation of all oocytes in one group (taking approximately 10 minutes), they were transferred into cytochalasin B-free CZB and held there for up to 2 hours at 37.5° C., to be returned to the microscope stage immediately prior to further manipulation.

For injection of donor nuclei into the enucleated oocytes prepared as described above, a microinjection chamber was prepared by employing the cover (approximately 5 mm in depth) of a plastic dish (100 mm×15 mm; Falcon Plastics, Oxnard, Calif., catalogue no. 1001). A row consisting of two round droplets and one elongated drop was placed along the center line of the dish. The first droplet (approximately 2 μL; 2 mm in diameter) was for pipette washing (Hepes-CZB containing 12% [w/v] PVP, average molecular weight, 360,000 daltons). The second droplet (approximately 2 μL; 2 mm in diameter) contained a suspension of donor cells in Hepes-CZB. The third elongated droplet (6 μL, 2 mm wide and 6 mm long) was of Hepes-CZB medium for the oocytes. Each of these droplets were covered with mineral oil (Squibb and Sons). The dish was placed on the stage of an inverted microscope with Hoffman Modulation contrast optics.

Microinjection of donor cell nuclei into oocytes was achieved by the piezo electric microinjection method described previously. Nuclei were removed from their respective somatic cells and subjected to gentle aspiration in and out of the injection pipette (approximately 7 μm inner diameter) until their nuclei became largely devoid of visible cytoplasmic material. Each nucleus was injected into a separate enucleated oocyte within 5 minutes of its isolation.

For injection, the nucleus was sucked deeply into the pipette. A small volume (about 0.5 μL) of mercury was placed near the proximal end of the injection pipette, which was then connected to the piezo electric-driven unit described above. After the mercury had been pushed towards the tip of the pipette, a small volume of medium (approximately 10 μL) was sucked into the pipette.

An enucleated oocyte was positioned on a microscope stage in a drop of CZB medium containing 5 μg/mL cytochalasin B. The oocyte was held by a holding pipette while the tip of the injection pipette was brought into intimate contact with the zona pellucida. Several piezo pulses (e.g., intensity 1–2, speed 1–2) were given to advance the pipette while a light negative pressure was applied within it. When the tip of the pipette had passed through the zona pellucida, the cylindrical piece of the zona in the pipette was expelled into the perivitelline space. After the donor nucleus was pushed forward until it was near the tip of the injection pipette, the pipette was advanced mechanically until its tip almost reached the opposite side of the oocyte's cortex. The oolemma was punctured by applying 1 or 2 piezo pulses (typically, intensity 1–2, speed 1) and the nucleus was expelled into the ooplasm with a minimum volume (about 6 pL) of accompanying medium. Sometimes, as much as possible of the medium was retrieved. The pipette was then gently withdrawn, leaving the nucleus the ooplasm. Each oocyte was injected with one nucleus. Approximately 5–20 oocytes may be microinjected by this method within 10–15 minutes. All injections were performed at room temperature usually in the range of 23°–28° C.

FIG. 1B illustrates a cumulus cell nucleus in an enucleated oocyte within 10 minutes of injection.

The nuclei of Sertoli cells and brain cells, prepared as described in Example 2, were also injected by piezo electric microinjection into enucleated oocytes, by the method described above for the injection of cumulus cells.

Some oocytes containing an injected nucleus were then immediately activated as described in Example 4. Other similar oocytes were incubated for a time period of up to about hours prior to activation.

Example 4

Oocyte Activation

Following somatic cell nucleus injection, some groups of oocytes were placed immediately in $Ca^{2+}$-free CZB containing both 10 mM $Sr^{2+}$ and 5 pg/mL cytochalasin B for 6 hours. Additional groups of enucleated oocytes injected with cumulus cell nuclei were left in CZB at 37.5° C. under 5% (v/v) $CO_2$ in air for 1 to 6 hours before removing to $Ca^{2+}$-free CZB containing both 10 mM $Sr^{2+}$ and 5 μ/mL cytochalasin B for 6 hours for activation. $Sr^{2+}$ treatment activated the oocytes, while the cytochalasin B prevented subsequent polar body formation and, therefore, chromosome expulsion. Examination of enucleated oocytes injected with cumulus cell nuclei revealed that chromosome condensation had occurred within 1 hour following injection (see FIG. 1C). When, subsequent to 1 to 6 hours incubation in $Sr^{2+}$-free medium, oocytes were activated in culture medium containing $Sr^{2+}$ and cytochalasin B, their cumulus-derived chromosomes segregated (see FIG. 1D) to form structures resembling the pronuclei formed after normal fertilization (referred to here as pseudo-pronuclei). Examination of 47 such oocytes after fixation and staining showed that 64% had two pseudo-pronuclei (see FIGS. 1E and 1E') and 36% had three or more. Oocytes with distinct pseudo-pronuclei were considered activated. Due to the cytokinesis-blocking effect of cytochalasin B, no polar body was formed and, therefore, all chromosomes were retained within the oocyte, regardless of the number of pseudo-pronuclei. Chromosome analysis of 13 such oocytes fixed prior to the first cleavage (data not shown) revealed that 85% had a normal diploid chromosome number (2n=40).

Following the pre-activation and/or activation incubation periods, the eggs were cultured in cytochalasin B-free CZB medium for embryo development. All resulting embryos were transferred to $Sr^{2+}$-free, cytochalasin B-free CZB medium and incubation continued at 37.5° C. under 5% (v/v) $CO_2$ in air.

FIG. 1F illustrates live blastocysts produced following injection of enucleated oocytes with cumulus cell nuclei.

Example 5

Embryo Transfer

Where appropriate, 2–8 cell embryos or morulae/blastocysts were respectively transferred into oviducts or uteri of foster mothers (CD-1, albino) that had been respectively mated with vasectomized CD-1 males 1 or 3 days previously to synchronize embryonic developmental stages with that of the uterine endometrium. Following Cesarean section of recipient females at 18.5–19.5 dpc, live fetuses were raised by lactating foster mothers (CD-1).

Example 6

DNA Typing

DNA from the following control strains and hybrids was obtained from spleen tissue: C57BL/6J (B6), C3H/HeJ (C3), DBA/2J (D2), B6C3F1 and B6D2F1. DNA from the three cumulus cell donor females (B6C3F1), the three oocyte recipient females (B6D2F1), and the three foster females (CD-1) was prepared from tail tip biopsies. Total DNA from six B6C3F1-derived, cloned offspring was prepared from their associated placentas.

For the microsatellite markers D1Mit46, DS2Mit102, and D3Mit49, primer pairs (MapPairs) were purchased from Research Genetics (Huntsville, Ala.) and typing performed as previously described in Dietrich, W. et al., *Genetics* 131, 423–447 (1992), except that PCR reactions were carried out for 30 cycles and products were separated by 3% agarose gels (Metaphor) and visualized by ethidium bromide staining.

The identification of endogenous ecotropic murine leukemia provirus DNA sequences (Emv loci) was following hybridization of Pvull-digested genomic DNA to the diagnostic probe, pEc-B4, according to the method described in Taylor, B. A. and L. Rowe, *Genomics* 5, 221–232 (1989). Probe labeling, Southern blotting, and hybridization procedures were as previously described in Johnson, K. R. et al., *Genomics* 12, 503–509 (1992).

RESULTS

Cloning with cumulus cell nuclei. The preimplantation development of host enucleated oocytes injected with the nuclei from cumulus cells is illustrated in Table 1. Out of 182 oocytes subjected to an activating stimulus immediately after injection, 153 (84.1%) were successfully activated and survived. Of these 153 oocytes, 61 developed into morula/blastocysts in vitro. However, 474 (93.3%) out of 508 injected oocytes activated 1–3 hours after injection, and 151 (83.0%) out of 182 injected oocytes activated 3–6 hours after injection, were successfully activated and survived. Of these, 277 (58.4%) and 101 (66.9%), respectively, developed into morula/blastocysts in vitro. Therefore, significantly higher proportions of oocytes developed into morula/blastocysts in vitro when they were activated 1–6 hours after nucleus injection, as compared to oocytes activated immediately after injection ($p<0.005$), and the time interval between nucleus injection and oocyte activation in these experiments appears to affect the rate of oocyte development.

Figure 2:
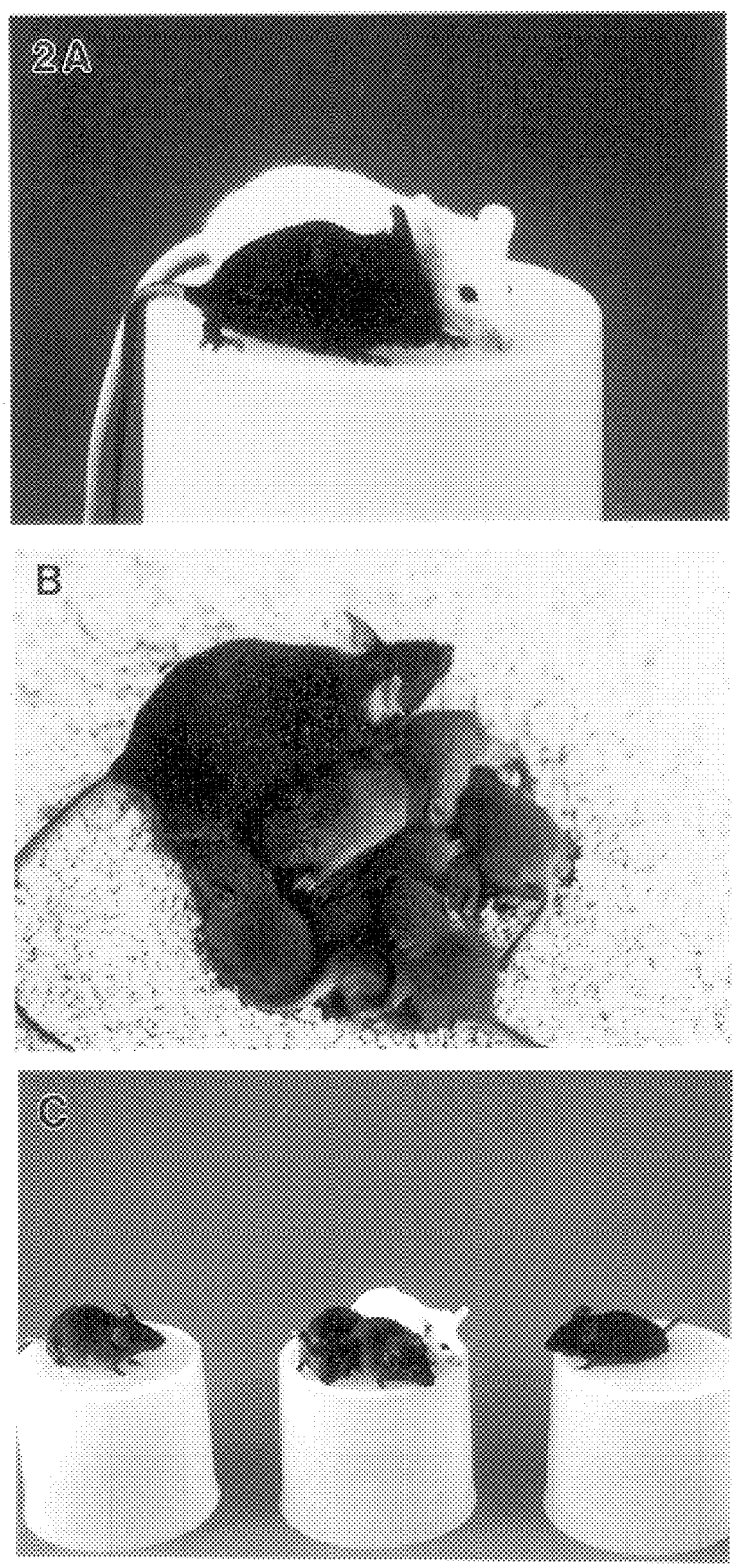
FIG. 2A is a photograph of four-week-old (cloned mouse) Cumulina (foreground) with her foster mother.
FIG. 2B is a photograph of Cumulina at 2.5 months with the pups she produced following mating with a CD-1 (albino) male.
FIG. 2C is a photograph of two B6C3F1-derived, cloned, agouti young (center) in front of their albino foster mother (CD-1), a B6D2F1 oocyte donor (black, right), and the B6C3F1 cumulus cell donor (agouti, left). The two agouti offspring in the center are clones (identical 'twin' sisters) of the agouti cumulus cell donor and are two of the offspring described in Series C (see text) and Table 2.

The development of host enucleated oocytes injected with the nuclei of cumulus cells is illustrated in Table 2. In the first series of experiments (Series A), a total of 142 developing embryos (at 2-cell to morula/blastocyst stage) were transferred to 16 recipient females. When these females were examined on day 8.5 and 11.5 day post coitum (dpc), 5 live and 5 dead fetuses were seen in uteri. In the second series of experiments (Series B), a total of 800 embryos were transferred into 54 foster mothers. When Cesarean sections were performed on 18.5–19.5 dpc, 17 live fetuses were found. Of these, 6 died soon after delivery, 1 died approximately 7 days after delivery, but the remaining 10 females survived and are apparently healthy. All of these, including the first-born (named "Cumulina", in the foreground of the photograph, FIG. 2A, with her albino foster mother) have been mated and delivered and raised normal offspring. FIG. 2B is a photograph of Cumulina at 2.5 months with the pups she produced following mating with a CD-1 (albino) male. Several of these offspring have, in turn, now developed into fertile adults.

In a third series of experiments (Series C in Table 2), B6C3F1 cumulus cell nuclei were injected into enucleated B6D2F1 oocytes. Whereas B6D2F1 mice are black, B6C3F1 mice carry a copy of the agouti A gene, and are consequently agouti. Offspring from this experiment should therefore have an agouti coat color, rather than the black of the B6D2F1 oocyte donors. A total of 298 embryos derived from B6C3F1 cumulus cell nuclei were transferred to 18 foster mothers. Cesarean sections performed 19.5 dpc revealed 6 live fetuses whose placentas were used in DNA typing analysis (see Example 6 above). Although 1 died a day after birth, the 5 extant females are healthy and have the agouti coat phenotype. FIG. 2C shows two such cloned agouti pups with their albino foster mother (CD-1) in the center of the photograph. To the left of the photograph is the corresponding agouti B6C3F1 cumulus donor. The cloned pups (center) are like the identical 'twin' sisters (i.e., they are the clones) of the cumulus donor. The B6D2F1 oocyte donor (black) is shown in the right of the photograph.

Additional experiments (Series D in Table 2) were performed to investigate whether clones could be efficiently cloned in subsequent rounds of recloning. In this experiment, cumulus cells were harvested from B6C3F1 (agouti) clones generated in Series C, and their nuclei were injected into enucleated B6D2F1 oocytes to generate embryos that were transferred as described for Series A–C. A total of 287 embryos derived from cloned B6C2F1 cumulus cell nuclei were transferred to 18 foster mothers. When Cesarean sections were performed 19.5 dpc, 8 live fetuses were recovered. Although 1 died soon after birth, the 7 surviving females are healthy and have the expected agouti coat phenotype. These results suggest that clones (Series B and C) and cloned clones (Series D) are produced with a similar efficiency. Subsequently, it has been possible to repeat the process using animals from Series D (data not shown) as cumulus chromosome donors, resulting in the birth of cloned cloned clones (third generation clones). Therefore, it appears that successive generations of clones do not undergo changes (either positive or negative) that influence the outcome of the cloning process.

Figure 4:
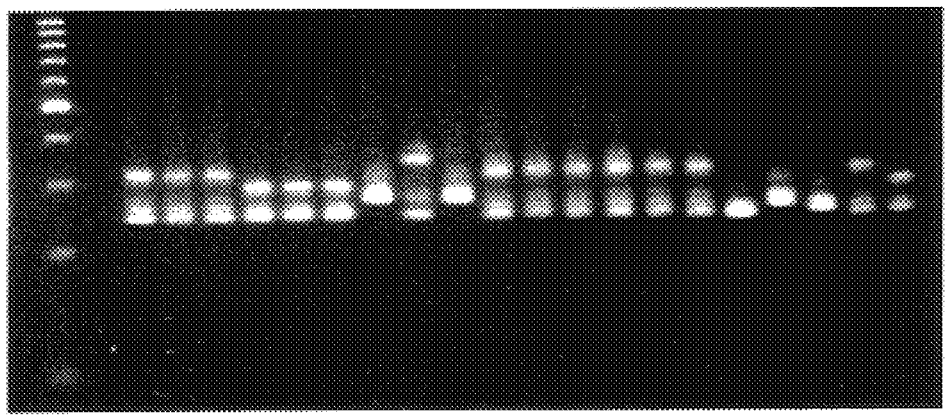
FIG. 4 represents DNA typing of donors and offspring in Series C (see text and Table 2) that corroborates genetic identity between cloned offspring and cumulus cell donors, and non-identity between oocyte donors and host foster females. Placental DNA from the six cloned Series C offspring (lanes 10–15) was compared with DNA from the three cumulus cell donor females (lanes 1–3), the three oocyte recipient females (lanes 4–6), and the three host females (lanes 7–9). Control DNA was from C57BL/6 (lane 16), C3H (lane 17), DBA/2 (lane 18), B6C3F1 (lane 19) and B6D2F1 (lane 20). 100 base pair (bp) DNA size marker ladders are shown on the left of FIGS. 4A and 4B.
Figure 4:
Figure 4:
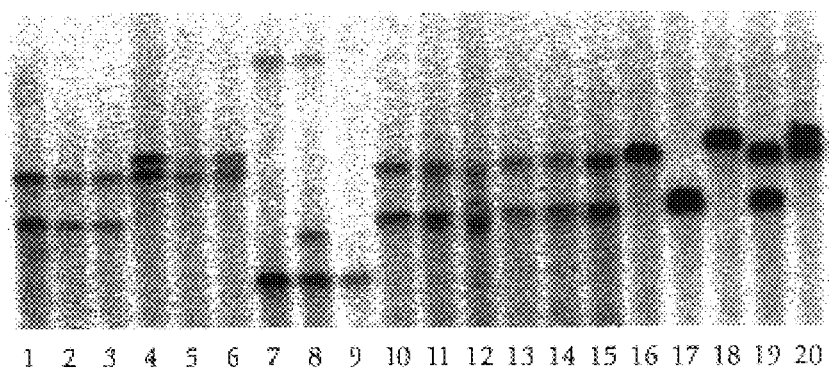

Confirmation of genetic identity of clones to cumulus cell donors. As illustrated in FIGS. 4A, 4B and 4C, DNA typing of donors and offspring in Series C corroborates the genetic identity of cloned offspring to cumulus cell donors, and non-identity to oocyte donors and host foster females. PCR typing of DNA was employed, using highly variable alleles (strain-specific markers) diagnostic of the C57BL/6, C3H, DBA/2 and CD-1 mouse strains. These strains, or their F1 hybrids, were used in this work and they therefore collectively account for all of the genotypes present. In all of the Figures, placental DNA from the six cloned Series C offspring (lanes 10–15) was compared with DNA from the three cumulus cell donor females (B6C3F1, lanes 1–3), the three oocyte donor females (B6D2F1, lanes 4–6), and the three host females (CD-1, lanes 7–9). Control DNA was from C57BL/6 (lane 16), C3H (lane 17), DBA/2 (lane 18), B6C3F1 (lane 19) and B6D2F1 (lane 20). FIGS. 4A and 4B illustrate the results of DNA typing employing agarose gels and the strain-specific markers D1Mit46 and D2Mit102, and FIG. 4C illustrates the results of DNA typing employing Southern blot analysis and the strain-specific Emv loci (Emv1, Emv2 and Emv3) markers.

The data presented in these Figures show genetic superimposability between cumulus nucleus donors and putative clones, and genetic non-identity with either the oocyte donors or the foster mothers. Therefore, the genome of each of the six cloned mice was derived from the nucleus of a cumulus cell.

That all of the live offspring reported here in Series B–D represent clones derived exclusively from the chromosomes of cumulus cells is confirmed in several ways. (1) The oocytes/eggs were not exposed to spermatozoa in vitro. (2) Foster mothers (CD-1, albino) were mated with vasectomized males (CD-1, albino) of proven infertility. In the unlikely event of fertilization by such a vasectomized male, the offspring would be albino. (3) The 2–8 cell embryos or blastocysts were transferred into oviduct/uteri of foster mothers. It is well established that 2–8 cell mouse embryos/blastocysts are totally refractory to fertilization by spermatozoa. (4) All term animals were born with black eyes. The surviving 10 from Series B have black coats and the surviving 5 in Series C have agouti coats. This pattern of coat color inheritance exactly matches that predicted by the genotype of the nucleus donor in each case. Since B6D2F1 mice lack the agouti A gene, the agouti mice in Series C must have inherited their agouti coat color from a non-B6D2F1 nucleus. (5) DNA typing of highly variable alleles diagnostic of the B6, C3, D2 and CD-1 strains used here (FIG. 4) demonstrates beyond reasonable doubt that the six cloned offspring in Series C (which includes one that died soon after birth) are isogeneic with the three cumulus cell donor females used (B6C3F1) and do not contain DNA derived from either the oocyte donors (B6D2F1) or host foster mothers (CD-1). (6) Following enucleation, extrusion of chromosomes into polar bodies was suppressed by using cytochalasin B. Thus, if enucleation of the oocytes had been totally unsuccessful or only partially successful, all embryos would have been hyperploid and would not have developed into normal offspring. (7) In mock experiments, in which 204 oocytes were enucleated and examined after fixation and staining, no chromosomes were apparent, suggesting the efficiency of chromosome removal exceeded 99.99%.

In Example 1, the cell type used was identified as the cumulus cell, with a high degree of certainty. The cells were not cultured in vitro. Ample time was given for cumulus nuclei to transform into condensed chromosomes within the cytoplasm of enucleated Met II oocytes. The rate of embryo development to morulae/blastocysts and implantation was very high. Prolonging the time between nuclear injection and oocyte activation was beneficial for both preimplantation and post-implantation development (see Tables 1 and 2) and may have enhanced the opportunity of cumulus cell genes to undergo reprogramming for embryonic development.

It is believed that the use of a piezo electric micromanipulator also contributed to a higher rate in embryonic development. This apparatus allowed manipulation of oocytes and donor cells (e.g., drilling the zona pellucida to enucleate the oocyte, and injecting of donor cell nuclei) to be performed very quickly and efficiently. Introduction of donor nuclei into oocytes using a piezo electric driven pipette appears to be less traumatic to the oocytes than the use of an electric pulse, Sendai virus or polyethylene glycol, and allows for introduction of the somatic cell nucleus directly into the cytoplasm of the oocyte. Also, the amount of somatic cell cytoplasm introduced into enucleated oocytes was minimized by microinjection. This may also have contributed to the high preimplantation development of embryos in the present invention.

Figure 3:
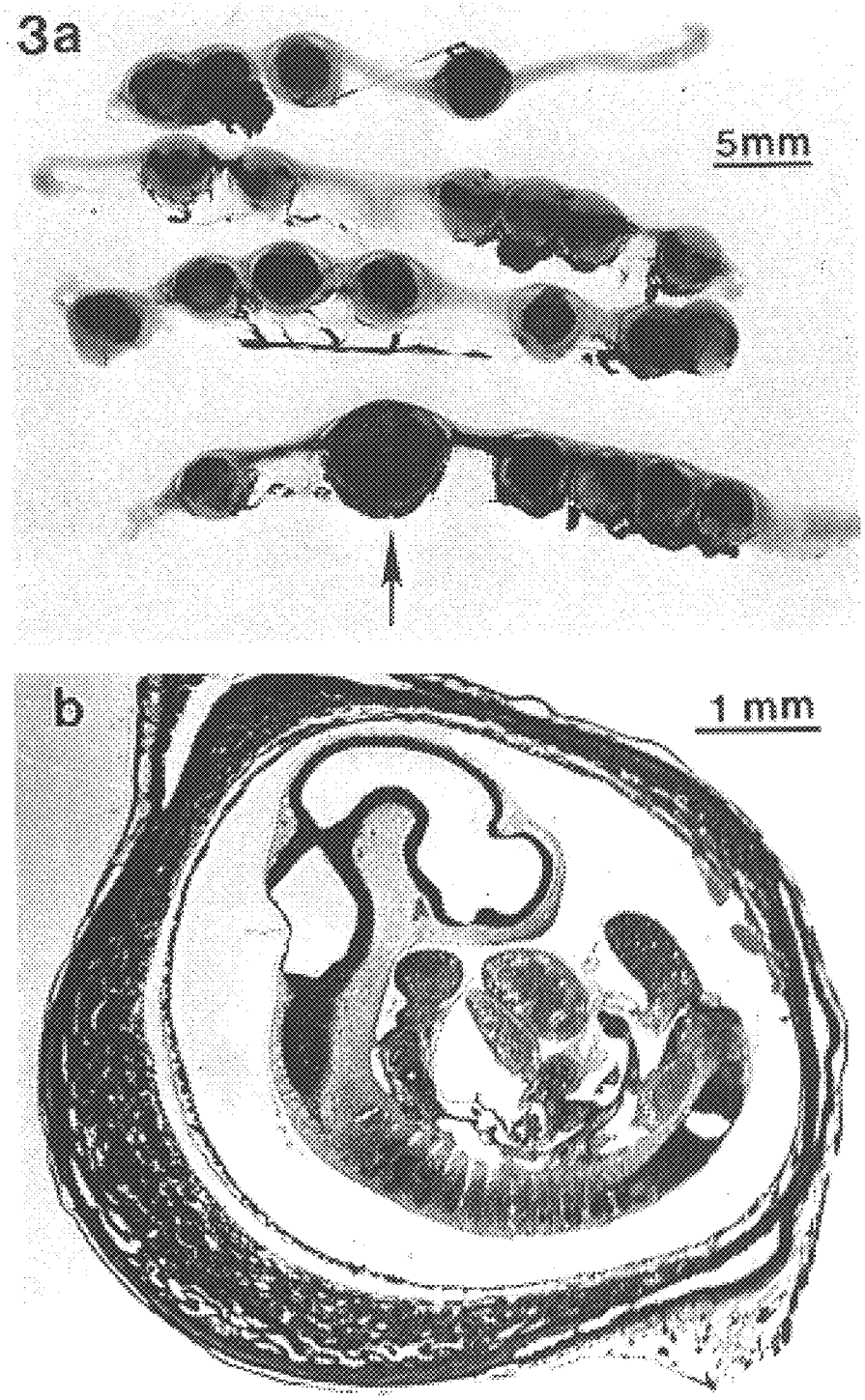
FIG. 3 illustrates the development following uterine transfer of embryos derived following injection of Sertoli cell nuclei into enucleated oocytes.

Cloning with Sertoli and brain cell nuclei. About 63 (40%) and 50 (22%) of enucleated oocytes injected with Sertoli cell nuclei and brain cell nuclei, respectively, developed into morulae/blastocysts in vitro and, of these 59 and 46, respectively were transferred to uteri of recipient foster mothers. FIG. 3 illustrates development of transferred embryos following injection of Sertoli cell nuclei into enucleated oocytes. FIG. 3A is a photograph of the uteri of recipient at 8.5 dpc. However, all uterine implantation sites failed to develop except for one live fetus (FIG. 3B) was found in the uterus of a foster mother euthanized 8.5 dpc (Table 3). None of the enucleated oocytes injected with brain cell nuclei developed beyond 6–7 dpc (Table 3).

Thus, the method of the invention provided embryonic and fetal development of oocytes injected with the nuclei of Sertoli cells or brain cells.

While the invention has been described herein with reference to the preferred embodiments, it is to be understood that it is not intended to limit the invention to the specific forms disclosed. On the contrary, it is intended to cover all of the manifold modifications and alternative forms falling within the spirit and scope of the invention.

TABLE 1

Preimplantation Development of Enucleated Eggs Injected With Cumulus Cell Nuclei

| Time of oocyte activation | Total No. of oocytes used | No. of enucleated oocytes | No. of surviving oocytes after injection | No. (%) of activated oocytes | No. (mean % ± SD) of embryo developed from activated oocytes, at 72 h after activation | | |
|---|---|---|---|---|---|---|---|
| | | | | | 1-cell and abnormal | 2 to 8-cell | Morula/Blastocyst |
| Simultaneously with injection | 233 | 230 | 182 | 153 (84.1) | 17 | 75 | 61 (39.9 ± 16.6)[a] |
| 1–3 hour after injection | 573 | 565 | 508 | 474 (93.3) | 20 | 177 | 277 (58.4 ± 12.6)[b] |
| 3–6 hour after injection | 195 | 191 | 182 | 151 (83.0) | 9 | 41 | 101 (66.9 ± 14.4)[b] |

Superscripts a or b within the same column indicate significant difference between ($P < 0.005$). The data were analyzed by the Chi-square test.

TABLE 2

Postimplantation Development of Enucleated Eggs Injected With Cumulus Cell Nuclei

| Exp. series.* | Time of oocyte activation | No. injected oocyte | No. transferred embryos (Recipients) | No. (%) implantation from transferred embryos† | Total (%)† | No. fetuses developed from transferred embryos 8.5 dpc Live | 8.5 dpc Dead | 11.5 dpc Live | 11.5 dpc Dead | No. (%) newborn from transferred embryos |
|---|---|---|---|---|---|---|---|---|---|---|
| A | Simultaneously with injection | 82 | 34 (4) | 8 (23.5)$^a$ | 0$^a$ | | | | | — |
|   | 1–3 hours after injection | 136 | 45 (5) | 32 (71.1)$^b$ | 7 (15.6)$^b$ | 3 | 2$^‡$ | 2 | 0 | — |
|   | 3–6 hours after injection | 124 | 63 (7) | 36 (57.1)$^b$ | 3 (4.8)$^b$ | 0 | 2$^{‡‡}$ | 0 | 1$^{‡‡‡}$ | — |
| B | 1–3 hour after injection | 1345 | 760 (49) | — | — | — | — | — | — | 16 (2.1) |
|   | 3–6 hour after injection | 62 | 40 (5) | — | — | — | — | — | — | 1 (2.5) |
| C | 1–3 hour after injection | 458 | 298 (18) | — | — | — | — | — | — | 6 (2.0) |
| D | 1–3 hour after injection | 603 | 287 (18) | — | — | — | — | — | — | 8 (2.8) |

*Series A, Cesarean section were performed on 8.5 dpc or 11.5 dpc;
Series B and C, Cesarean section were performed on 18.5–19.5 dpc.
In Series A and B, each donor nucleus is from a B6D2F1 cumulus cell.
In Series C, each donor nucleus is from a B6C2F1 cumulus cell.
In Series D, each donor nucleus is from a B6C3F1 cloned mouse from Series C.
†Superscripts a and b within the same column indicate significant difference between a and b: implantation ($P < 0.005$); fetal development ($P < 0.05$). The data were analyzed by Chi-square tests.
‡Died 6–7 dpc;
‡‡Died 7–8 dpc;
‡‡‡Died 10 dpc

TABLE 3

Development of Enucleated Eggs Injected With Sertoli or Brain Cell Nuclei*

| Cell type injected | No. of surviving oocytes injected | No. (%) of oocytes activated | Total no. (%) of morulae/ blastocyst developed | No. transferred embryos (Recipient) | Implantation sites | Fetuses |
|---|---|---|---|---|---|---|
| Sertoli | 159 | 159 (100) | 63 (39.6)$^a$ | 59 (8) | 41 (69.5) | 1 (1.7) |
| Brain | 228 | 223 (97.8) | 50 (22.4)$^b$ | 46 (5) | 25 (54.3) | 1 (2.2)† |

*All recipients were euthanized at 8.5 dpc. Superscripts a or b within the same column indicate a significant difference ($P <0.005$) between and b.
†Died about 6 to 7 dpc

We claim:

1. A method for cloning a non-human mammal comprising the steps of:
   (a) collecting a nucleus from a cumulus cell of an adult non-human mammal;
   (b) inserting at least a portion of the nucleus that includes the chromosomes into an enucleated oocyte to form a renucleated oocyte;
   (c) allowing the renucleated oocyte to develop into an embryo; and
   (d) allowing the embryo to develop into a live offspring.

2. The method of claim 1, wherein the nucleus is collected from a cumulus cell that has 2n chromosomes.

3. The method of claim 1, wherein the nucleus is collected from a cumulus cell that is 2C to 4C.

4. The method of claim 1, wherein the nucleus is inserted into the cytoplasm of the enucleated oocyte.

5. The method of claim 4, wherein the inserting step is accomplished by microinjection.

6. The method of claim 5, wherein the microinjection is piezo electrically-actuated microinjection.

7. The method of claim 1, wherein the enucleated oocyte is arrested in the metaphase of the second meiotic division.

8. The method of claim 1, further comprising the step of activating the oocyte prior to, or during, or after the insertion of the nucleus.

9. The method of claim 8, wherein the activation step takes place from zero to about six hours after the insertion of the nucleus.

10. The method of claim 8, wherein the activation step takes place prior to insertion of the nucleus.

11. The method of claim 8, wherein the activation step comprises electroactivation, or exposure to a chemical activating agent.

12. The method of claim 11, wherein the chemical activating agent is selected from the group consisting of ethyl alcohol, sperm cytoplasmic factors, oocyte receptor ligand peptide mimetics, pharmacological stimulators of $Ca^{2+}$ release, $Ca^{2+}$ ionophores, strontium ions, modulators of phosphoprotein signaling, inhibitors of protein synthesis, and combinations thereof.

13. The method of claim 12, wherein the chemical activating agent is selected from the group consisting of caffeine, the $Ca^{2+}$ ionophore A 23187, ethanol, 2-aminopurine, staurospurine, sphingosine, cyclohexamide, ionomycin, 6-dimethylaminopurine, and combinations thereof.

14. The method of claim 12, wherein the activating agent comprises $Sr^{2+}$.

15. The method of claim 1, further comprising the step of disrupting microtubule formation in the oocyte for a time interval prior to or after insertion of the nucleus.

16. The method of claim 15, wherein the time interval is zero to about 6 hours.

17. The method of claim 15, wherein the microtubule formation is disrupted by a selection from the group consisting of cytochalasin B, nocodazole, colchicine, and combinations thereof.

18. The method of claim 17, wherein the microtubule formation is disrupted by cytochalasin B.

19. The method of claim 1, further comprising the step of disrupting actin filaments in the oocyte for a time interval prior to or after insertion of the nucleus.

20. The method of claim 19, wherein the time interval is from about zero to about 6 hours.

21. The method of claim 20, wherein the actin filaments are disrupted by cytochalasin D, jasplakinolide, latrunculin A, or combinations thereof.

22. The method of claim 1, wherein the step of allowing the embryo to develop into a live offspring further comprises the substep of transferring the embryo to a female surrogate recipient, wherein the embryo develops into a viable fetus.

* * * * *